United States Patent [19]

Osterburg et al.

[11] Patent Number: 5,132,476
[45] Date of Patent: Jul. 21, 1992

[54] PROCESS FOR PRODUCING $C_3$-$C_4$ MONOALKYLCHLORIDES

[75] Inventors: Gunther Osterburg, Rheurdt; Wolfgang Reith, Geldern; Karl-Heinz Gluzek, Alpen, all of Fed. Rep. of Germany

[73] Assignee: RWE-DEA Aktiengesellschaft fuer Mineraloel und Chemie, Fed. Rep. of Germany

[21] Appl. No.: 719,660

[22] Filed: Jun. 24, 1991

Related U.S. Application Data

[63] Continuation-in-part of Ser. No. 508,232, Apr. 12, 1990, abandoned.

[30] Foreign Application Priority Data

Apr. 13, 1989 [DE] Fed. Rep. of Germany ....... 3912094

[51] Int. Cl.$^5$ .............................................. C07C 17/16
[52] U.S. Cl. .................................................. 570/258
[58] Field of Search ......................................... 570/258

[56] References Cited

U.S. PATENT DOCUMENTS 2,516,638  7/1950  McCurdy ............................. 570/258
4,220,604  9/1980  McEntee et al. .................... 570/258

Primary Examiner—Howard T. Mars
Attorney, Agent, or Firm—Thomas H. Whaley

[57] ABSTRACT

The vaporous reaction product from the continuous reaction of $C_3$-$C_4$ monoalkanols with hydrogen chloride is removed, condensed, and split into a light organic phase and a heavy aqueous phase. The heavy aqueous phase is immediately distilled yielding HCl-containing reaction water at the bottom of the column and an alcohol stream at the head of the column from where it is returned to the synthesis. The light organic phase is washed with water, dried and, optionally, distilled. The water from this washing operation is neutralized, stripped off in order to remove dissolved organic constituents, and removed as waste water from the system.

5 Claims, 1 Drawing Sheet

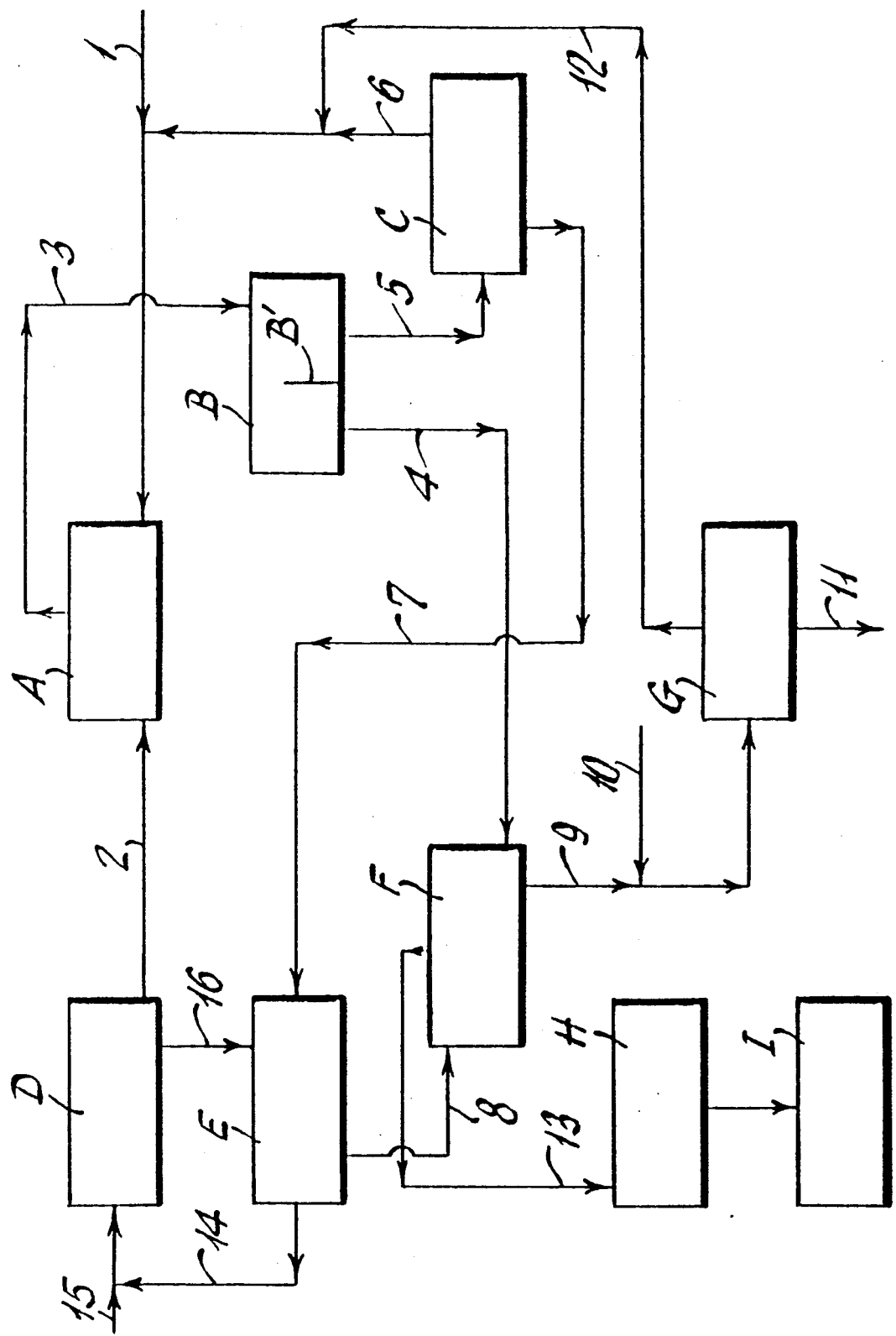

PROCESS FOR PRODUCING $C_3$-$C_4$ MONOALKYLCHLORIDES

This application is a continuation-in-part of U.S. patent application, Ser. No. 508,232, filed Apr. 12, 1990 now abandoned.

The present invention relates to a process for working up the product from the continuous reaction of $C_3$-$C_4$ monoalkanols with hydrogen chloride at elevated temperature and, optionally, in the presence of a catalyst for producing $C_3$-$C_4$ monoalkylchlorides by stripping off the vaporous reaction product, purifying and separating the alkyl chloride by washing with water, drying, and, optionally, distilling the crude alkyl chloride.

Alkyl chlorides can be produced by reacting the corresponding alkanols with hydrogen chloride at elevated temperature and, preferably, in the presence of catalysts.

The German patent specification 24 22 969 describes a process for the separation of $C_1$-$C_3$ chloroalkanes from mixtures produced by reacting $C_1$-$C_3$ alkanols with hydrogen chloride whereby superheated vapor consisting of chloroalkane, the unreacted starting materials alkanol and hydrogen chloride, and water is obtained. According to said patent specification, the superheated vapor is treated in a distillation column with an aqueous solution of alkali hydroxide binding most of the hydrogen chloride present, the solution obtained is removed, the descending alkyl chloride vapor is led into an alkali purifying column where it is washed with alkali hydroxide at 10° to 50° C. while binding the remaining hydrogen chloride, the solution obtained from this washing operation is returned for treating the superheated vapor, the purified alkyl chloride vapor is fed into a cooled packed column where the unreacted alkanol is liquefied and removed and the alkyl chloride is isolated as known per se.

The unreacted alcohol on the one hand and the reaction water on the other hand can only be separated by simultaneous neutralization of the HCl contained therein with aqueous alkaline solution. Besides the loss of unreacted HCl resulting therefrom, salt-containing waste water is obtained in varying quantities, depending on the conversion. Prior to purification this waste water must be freed from organic components in a stripping column.

It was the object of the invention to develop a continuous process that does not have the disadvantages of the described prior art and that allows, in particular, to isolate and reuse the unreacted HCl while avoiding formation of salt-containing waste water.

According to the invention, this problem is solved by condensing the vaporous reaction product, splitting it into a light organic phase and a heavy aqueous phase, distilling immediately the heavy aqueous phase whereby reaction water containing not more than 21% HCl is obtained at the bottom of the column and an alcohol stream containing HCl and water is obtained at the head of the column, returning the alcohol stream together with the feed alcohol to the synthesis, washing the light organic phase with water, neutralizing and stripping the water in order to remove dissolved organic components, and removing it from the system.

According to a preferred embodiment of this invention, the HCl-containing reaction water is split into hydrogen chloride and water, the hydrogen chloride is returned to the synthesis, and the water which is optionally adjusted at a pH-value of equal to/less than 8 is used for washing the alkyl chloride.

According to the invention, the unreacted alcohol and HCl are separated from the reaction water by distillation in a recycle column whereby at the head of the column alcohols containing HCl and water are obtained which are recycled to the alkyl chloride synthesis. The HCl and water content in the alcohols varies with the alcohol type. The reaction water containing not more than 21% HCl is removed at the bottom of the recycle column and may be led to the HCl production facility.

The process of the invention differs from the prior art in the following essential features:

In principle, it is prevented that the reactor effluent contacts alkali during working up. Both the back reaction of the alkyl chlorides and the contamination of hydrochloric acid are thus prevented.

The quantity of unreacted hydrogen chloride present in the heavy aqueous phase is reduced by direct recycling to the process and is limited to max. 21% in the reaction water.

The amount of hydrochloric acid produced is not greater than the amount of reaction water obtained. The hydrochloric acid is obtained in such purity allowing direct marketing or use in the production of hydrogen chloride.

In the latter application the remaining reaction water can be used for extracting the HCl and alcohol remainders from the alkyl chloride. Thus, the fresh water feed and the waste water quantity can be significantly reduced.

The separation process as a whole makes allowance for the azeotropic correlation between alkyl chlorides and alcohols increasing with increasing C-numbers as well as for the pecularities of the selectivities of the different alkyl chloride syntheses.

The reaction product worked up according to the invention is obtained by reacting the corresponding $C_3$ or $C_4$ monoalkanols with hydrogen chloride in the presence of a customary catalyst, e.g. zinc chloride at elevated temperature. Usually, the reaction temperature at atmospheric pressure is about 100° to 180° C., preferably 100° to 150° C. The crude gaseous reaction product thus obtained contains unreacted hydrogen chloride, unreacted alcohol, alkyl chloride, water, the corresponding dialkyl ethers, and olefins.

An embodiment of the process according to the invention is shown in figure and is described in the following:

Fresh alcohol is fed via line 1, optionally after passing through an offgas scrubber (not depicted), together with the alcohol recycle from line 6 and hydrogen chloride from line 2 at a mole ratio of 1:1 to the bottom of reactor A designed as a reboiler.

Suitable reaction conditions are described in U.S. Pat. No. 4,220,609 to McEntee, et al, incorporated herein by reference.

As catalyst solution a 60 to 70% solution of zinc chloride in water is present in the reactor, the catalyst quantity depending on the synthesis conditions determined by the maximum catalyst load envisaged.

The reaction temperature in reactor A is adjusted according to conversion and selectivity required for the respective alkyl chloride to be produced. The vaporous reaction product consisting of alkyl chloride, water, by-products as well as unreacted alcohol and HCl is removed from the reactor via line 3, is condensed, and is split in separator B into a light organic phase containing the alkyl chloride and a heavy aqueous phase.

The lighter liquid organic phase is separated from the immiscible heavier liquid aqueous phase by gravity in known manner. As illustrated diagrammatically in the figure, separator B is divided into two compartments. Condensate from line 3 enters one compartment from which the heavier aqueous liquid phase is withdrawn through line 5. The lighter organic liquid phase overflows divider B' into the other compartment and is withdrawn through line 4.

The heavy aqueous phase is fed via line 5 directly into recycle column C from the bottom of which the reaction water is normally removed through line 7 as a maximum boiling point water/HCl azeotrope containing 21 wt. % HCl. The hydrogen chloride in the reaction water is returned to the synthesis feed via the second stage E of the HCl production facility D/E. All the other constituents of the heavy aqueous phase, such as alcohol, alkyl chloride, azeotropic water, and the remaining unreacted hydrogen chloride are separated as overhead product and are returned to the synthesis via line 6 as azeotropic alcohol recycle together with fresh alcohol. Small quantities of HCl gas from the reflux drum of recycle column C as well as the gas possibly obtained from separator B of the alkyl chloride synthesis are absorbed by the feed alcohol in the offgas scrubber (not depicted) and are returned to the synthesis.

The crude alkyl chloride from separator B that contains small amounts of the unreacted alcohol and hydrogen chloride as well as water and the by-products of the respective synthesis is fed unchanged via line 4 into the multistage counterflow extractor F where it is washed. The water for extraction may be condensate which should be used together with the neutralized waste water removed via line 8 from the HCl production facility D/E. The pH-value of the water should not exceed 8.

Hydrogen chloride is recovered for recycle to reactor A by passing the water/HCl azeotrope from recycle column C to distillation zone E by way of line 7. In distillation zone E, maintained for example, at a pressure of about 0.1 bar, water is distilled from the water/HCl mixture and passed through line 8 to extractor F. A maximum boiling mixture of water and HCl in the form of an azeotrope containing about 30 weight percent HCl is obtained, which is passed through line 14 to distillation zone D of the HCl production facility where it is admixed with commercial hydrochloric acid from line 15 containing approximately 30 weight percent HCl in water. In distillation zone D, suitably maintained at a pressure in the range of 1 to 3 bar, substantially anhydrous HCl is distilled from a water/HCl mixture. A maximum boiling mixture of water and HCl is obtained in zone D containing approximately 20 weight percent HCl as a water/HCl azeotrope. The water/HCl azeotrope from distillation zone D is passed through line 16 to distillation zone E where it is concentrated to 30 weight percent HCl as a water/HCl azeotrope and returned to distillation zone D through lines 14 and 15.

The extract phase, i.e. the water from this washing operation, is then removed through line 9, neutralized with NaOH from line 10, and freed in stripping column G from dissolved organic constituents, such as alcohol and alkyl chloride. The organic constituents are fed via line 12 to the azeotropic alcohol recycle in line 6 from recycle column C and are fed with the fresh alcohol into the synthesis. The neutralized wash water freed from dissolved organic constituents is fed via line 11 to the waste water.

The alcohol remainder in the pure alkyl chloride can be adjusted by the wash water/alkyl chloride ratio depending on the respective partition coefficients.

The purifying distillation of the alkyl chloride is carried out as generally known in two continuously operating distillation columns, light-end column H and heavy-end column I. Different ways may be chosen depending on the type of product and the by-product content.

Before distilling the washed, still moist alkyl chloride removed via line 13 from counterflow extractor F, drying in an absorber (not depicted) may be advisable in order to prevent corrosion in the first distillation column. If drying of the alkyl chloride is considered unnecessary, the water can be separated instead by azeotropic distillation in the first column H.

The following examples illustrate the process according to the invention. The results of the examples are set forth in Table I.

EXAMPLE 1

Catalyst solution in an amount of 1.0 mole = 136.3 g of zinc chloride (dissolved at 70% in water) was placed in a glass reactor having an inside diameter of 40 mm and a length of 550 mm and wrapped up to a height of 280 mm in an oil-heated jacket. The heating oil recycle in the jacket was adjusted such that the temperature of the catalyst solution was maintained at 127° C. N-butyl alcohol in an amount of 3 moles = 220 g, 3.4 moles = 124 g of hydrogen chloride, and 318 g of azeotropic alcohol from the recycle column were then fed per hour to the bottom of the reactor. At the same time 649 g of vaporous reaction product were removed from the reactor head and were condensed. The reaction product was removed and split in a separator into 267 g of a light organic phase and 382 g of a heavy aqueous phase which were further transported separately.

The heavy aqueous phase was fed directly and continuously into the recycle column where the aqueous phase was split by distillation at a head temperature of 98.5° C. and a bottom temperature of 110° C. such that at the column head 318 g of azeotropic recycle alcohol were obtained which were immediately fed into the reactor and at the bottom of the reactor 64 g of a 21% hydrochloric acid were obtained.

Except for the hydrogen chloride in the product obtained at the bottom of the recycle column, which can be recuperated in HCl reconcentration columns, the total excess of HCl necessary for the synthesis as well as the unreacted alcohol were recycled to the synthesis in the presence of water.

The light organic phase was continuously fed into the counterflow extractor where it was treated with water. The resulting crude alkyl chloride which was free from alcohol and salt was then distilled in a light-end and a heavy-end column.

Finally, only the sodium hydroxide neutralized wash water from the counterflow extractor was removed in the stripping column.

EXAMPLE 2

Example 1 was repeated, the difference being that 4 moles = 295 g of n-butyl alcohol, 4.5 moles = 165 g of hydrogen chloride and 549 g of azeotropic recycle alcohol were fed per hour into the reactor. At a reaction temperature of 127° C. 993 g of vaporous reaction product were removed and condensed. In the separator the product separated into 359 g of light organic phase and 634 g of heavy aqueous phase. In the recycle column the aqueous phase was split into 549 g of azeotropic recycle alcohol and 85 g of 21% hydrochloric acid.

EXAMPLE 3

Example 1 was repeated, the difference being that 4.5 moles = 333 g of n-butyl alcohol, 5.1 moles = 186 g of hydrogen chloride and 466 g of azeotropic recycle alcohol were fed per hour into the reactor. At a reaction temperature of 130° C. 968 g of vaporous reaction product were removed and condensed. In the separator the product separated into 405 g of light organic phase and 563 g of heavy aqueous phase. In the recycle column the heavy aqueous phase was split into 466 g of azeotropic recycle alcohol and 97 g of 21% hydrochloric acid.

EXAMPLE 4

Example 1 was repeated, the difference being that 5.5 moles = 408 g of n-butyl alcohol, 6.2 moles = 227 g of hydrogen chloride and 558 g of azeotropic recycle alcohol were fed per hour into the reactor. At a reaction temperature of 133° C. 1172 g of vaporous reaction product were removed and condensed. In the separator the product separated into 495 g of light organic phase and 677 g of heavy aqueous phase. In the recycle column the aqueous phase was split into 558 g of azeotropic recycle alcohol and 119 g of 21% hydrochloric acid.

EXAMPLE 5

Example 1 was repeated, the difference being that 10 moles = 739 g of sec-butyl alcohol, 10 moles = 365 g of hydrogen chloride and 91.4 g of azeotropic recycle alcohol were fed per hour into the reactor. At a reaction temperature of 120° C. 1200 g of vaporous reaction product were removed and condensed. In the separator the product separated into 886 g of light organic phase and 314 g of heavy aqueous phase. In the recycle column the heavy aqueous phase was split into 91.4 g of azeotropic recycle alcohol and 222 g of 21% hydrochloric acid.

EXAMPLE 6

Example 1 was repeated, the difference being that 15 moles = 900 g of isopropyl alcohol, 16 moles = 584 g of hydrogen chloride and 62 g of azeotropic recycle alcohol were fed per hour into the reactor. At a reaction temperature of 118° C. 1546 g of vaporous reaction product were removed and condensed. In the separator the product separated into 1170 g of light organic phase and 376 g of heavy aqueous phase. In the recycle column the heavy aqueous phase was split into 62 g of azeotropic recycle alcohol and 314 g of hydrochloric acid with 15.6% HCl.

The low HCl excess with good conversion is attributable to the reactivity of the isopropyl alcohol. For this reason the recycle alcohol in this example is free from HCl and the HCl concentration in the reaction water effluent is less than 21%.

|  |  | Example 1 | Example 2 | Example 3 | Example 4 | Example 5 | Example 6 |
|---|---|---|---|---|---|---|---|
| Temperature | °C. | 127 | 127 | 130 | 133 | 120 | 118 |
| Reactor feed |  |  |  |  |  |  |  |
| NBA | g/h | 220 | 295 | 333 | 408 |  |  |
| SBA | g/h |  |  |  |  | 739 |  |
| IPA | g/h |  |  |  |  |  | 900 |
| HCl | g/h | 124 | 165 | 186 | 227 | 365 | 584 |
| Reactor effluent, aqueous organic phase |  | 1.4 | 1.8 | 1.4 | 1.4 | 0.4 | 0.3 |
| Organic phase | g/h | 267 | 359 | 405 | 495 | 886 | 1170 |
| Olefins | wt. % | 0.7 | 0.6 | 0.8 | 1.2 | 5.9 | 0.4 |
| IPC | wt. % |  |  |  |  |  | 97.9 |
| SBC | wt. % | 12.5 | 8.3 | 12.3 | 14.9 | 92.6 |  |
| NBC | wt. % | 80.7 | 82.5 | 79.7 | 76.8 |  |  |
| Ethers + Dimers | wt. % | 4.6 | 6.3 | 5.4 | 4.9 | 0.1 | 0.2 |
| NBA | wt. % | 1.0 | 1.3 | 1.1 | 1.2 |  |  |
| SBA | wt. % |  |  |  |  | 1.4 |  |
| IPA | wt. % |  |  |  |  |  | 1.3 |
| HCl | wt. % | 0.5 | 1.0 | 0.7 | 1.0 |  | 0.2 |
| Aqueous phase | g/h | 382 | 634 | 563 | 677 | 314 | 376 |
| SBC | wt. % | 0.8 | 0.7 | 0.7 | 1.0 | 0.7 |  |
| NBC | wt. % | 4.7 | 5.8 | 5.7 | 4.4 |  |  |
| Ethers + Dimers | wt. % | 1.2 | 1.7 | 1.7 | 1.3 |  |  |
| NBA | wt. % | 35.0 | 34.7 | 34.2 | 33.0 |  |  |
| SBA | wt. % |  |  |  |  | 18.2 |  |
| IPA | wt. % |  |  |  |  |  | 14.4 |
| Water | wt. % | 31.3 | 30.7 | 31.4 | 32.5 | 56.2 | 72.6 |
| HCl | wt. % | 27.0 | 26.4 | 26.3 | 27.8 | 24.9 | 13.0 |
| Recycle to reactor | g/h | 318 | 549 | 466 | 558 | 91 | 62 |
| SBC | wt. % | 0.9 | 0.8 | 0.8 | 1.2 | 33.9 |  |
| NBC | wt. % | 8.6 | 8.7 | 8.7 | 7.3 |  |  |
| Ethers + Dimers | wt. % | 1.4 | 2.1 | 2.2 | 1.6 |  |  |
| NBA | wt. % | 41.3 | 39.7 | 39.8 | 39.3 |  |  |
| SBA | wt. % |  |  |  |  | 37.2 |  |
| IPA | wt. % |  |  |  |  |  | 87.1 |
| Water | wt. % | 22.9 | 22.6 | 22.5 | 23.1 | 6.1 | 12.9 |
| HCl | wt. % | 24.9 | 26.1 | 26.0 | 27.5 | 22.8 |  |
| Alcohol conversion | % | 98.3 | 98.3 | 98.6 | 98.0 | 98.3 | 98.3 |
| Selectivity |  |  |  |  |  |  |  |
| IPC | % |  |  |  |  |  | 99.0 |
| SBC | % | 12.3 | 8.2 | 12.1 | 14.1 | 90.4 |  |

-continued

|  |  | Example | | | | | |
| --- | --- | --- | --- | --- | --- | --- | --- |
|  |  | 1 | 2 | 3 | 4 | 5 | 6 |
| NBC | % | 79.8 | 81.7 | 78.9 | 76.1 | | |
| Catalyst efficiency | mole/mole · h | 2.3 | 3.2 | 3.5 | 4.1 | 8.9 | 14.6 |

We claim:

1. In a process for the preparation of alkyl chlorides by the synthesis reaction of $C_3$–$C_4$ monoalkanols with HCl, the improvement which comprises:
   a) condensing the vaporous reaction product of the synthesis reaction forming a lighter liquid organic phase and an immiscible heavier liquid aqueous phase,
   b) separating the aqueous phase from the organic phase by gravity,
   c) distilling the aqueous phase effecting separation of a distillate fraction comprising unreacted alcohol from a maximum boiling azeotrope of water and HCl,
   d) recycling the distillate fraction comprising unreacted alcohol to the synthesis reaction, and
   e) separating HCl from the azeotrope of water and HCl from step c) and returning HCl to the synthesis reaction.

2. A process as defined in claim 1 wherein in the distillation of the aqueous phase in step c) a mixture of alcohol, alkyl chloride, water and HCl comprises the distillate fraction returned to the synthesis reaction.

3. In a continuous process for the production of $C_3$–$C_4$ monoalkylchlorides by catalytic reaction of a feed stream of $C_3$–$C_4$ monoalcohols with a feed stream of HCl in a synthesis reaction step with the concomitant production of water of reaction, the improvement which comprises condensing the vaporous reaction product forming a light liquid organic phase comprising alkyl chlorides and a heavy liquid aqueous phase, separating the organic liquid phase from the aqueous liquid phase by gravity; distilling the aqueous phase with the recovery of a maximum boiling azeotrope of water and HCl and a lower boiling mixture of unreacted alcohols containing HCl, alkyl chloride, and water; returning said lower boiling mixture to the synthesis reaction step; washing the light organic phase with water effecting removal of unreacted alcohols and HCl from the alkyl chloride product, neutralizing resulting wash water, stripping volatile organic compounds from the neutralized wash water; and discarding the thus decontaminated water of reaction from the process.

4. A process according to claim 1 or 3 wherein the reaction is carried out in the presence of a zinc chloride catalyst at substantially atmospheric pressure and at a temperature in the range of 100° C. to 150° C.

5. A process according to claim 3 wherein the wash water is water of reaction and the excess water of reaction is discarded following decontamination.

* * * * *